US008138323B2

(12) United States Patent
Wallach et al.

(10) Patent No.: US 8,138,323 B2
(45) Date of Patent: Mar. 20, 2012

(54) ISOLATED CDNA ENCODING TUMOR NECROSIS FACTOR BINDING PROTEIN II, ITS PURIFICATION, AND VECTORS, HOSTS AND PROCESSES USING SUCH CDNA

(75) Inventors: David Wallach, Rehovot (IL); Hartmut Engelmann, Munich (DE); Dan Aderka, Holon (IL); Daniela Novick, Rehovot (IL); Menachem Rubinstein, Givat Shmuel (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 1984 days.

(21) Appl. No.: 10/319,536

(22) Filed: Dec. 16, 2002

(65) Prior Publication Data

US 2003/0124675 A1    Jul. 3, 2003

Related U.S. Application Data

(60) Continuation of application No. 08/485,129, filed on Jun. 7, 1995, now abandoned, which is a division of application No. 07/930,443, filed on Aug. 19, 1992, which is a continuation of application No. 07/524,263, filed on May 16, 1990, now abandoned.

(30) Foreign Application Priority Data

May 18, 1989  (IL) .......................... 90339
Aug. 6, 1989  (IL) .......................... 91229
Apr. 6, 1990  (IL) .......................... 94039

(51) Int. Cl.
  *C12N 15/28*  (2006.01)
  *C12N 15/79*  (2006.01)
  *C12N 15/74*  (2006.01)
  *C12N 5/10*   (2006.01)
  *C12N 1/21*   (2006.01)

(52) U.S. Cl. ... 536/23.5; 435/69.1; 435/325; 435/320.1; 435/252.3

(58) Field of Classification Search .......................... None
See application file for complete search history.

(56) References Cited

U.S. PATENT DOCUMENTS 5,344,915 A  9/1994  LeMaire
5,395,760 A  3/1995  Smith et al.
5,605,690 A  2/1997  Jacobs et al.

FOREIGN PATENT DOCUMENTS

AU   897690        1/1991
EP   0418014 A1    3/1991
WO   WO 90/13575 A1  11/1990

OTHER PUBLICATIONS

Mimotopes, "Antipeptide Antibodies", May 10, 2001, www.alphagenix.com/antipep.pdf, retrieved Jan. 29, 2011.*
Balavoine et al, "Prostaglandin $E_2$ and collagenase production by fibroblasts and synovial cells is regulated by urine-derived human interleukin 1 and inhibitor(s)", *J Clin Invest* 78(4):1120-1124 (1986).
Beutler et al, "Passive Immunization against cachectin/tumor necrosis factor protects mice from lethal effect of endotoxin", *Science* 229(4716):869-871 (1985).
Beutler et al, "Cachectin: more than a tumor necrosis factor", *N Engl J Med* 316(7):379-385 (1987).
Beutler et al, *Tumor Necrosis Factors* . . . , Raven Press, new York, NY, pp. 145 and 383 (1992).
Brockhaus et al, "Monoclonal Antibodies against the TNF-Receptor Inhibit and Down-Regulate TNF Binding", 2$^{nd}$ Int'l Conference on Tumor Necrosis Factor and Related Cytokines, Jan. 15-20, 1989; WA 140.
Brockhaus et al, "Identification of two types of tumor necrosis factor receptors on human cell lines by monoclonal antibodies", *Proc Natl Acad Sci USA* 87(8):3127-3131 (1990).
Creasey et al, "Biological effects of recombinant human tumor necrosis factor and its novel muteins on tumor and normal cell lines" *Cancer Res* 47(1):145-149 (1987).
Engelmann et al, "Two tumor necrosis factor-binding proteins purified from human urine. Evidence for immunological cross-reactivity with cell surface tumor necrosis factor receptors" *J Biol Chem* 265(3):1531-1536 (1990).
Hohmann et al, "Two Different Cell Types Have Different Major Receptor Proteins for Human Tumor Necrosis Factor (TNFα)", 2$^{nd}$ Int'l Conference on Tumor Necrosis Factor and Related Cytokines, Jan. 15-20, 1989; WA 140.
Homann et al, "Two different cell types have different major receptors for human tumor necrosis factor (TNF-α)", *J Biol Chem* 264(25):14927-14934 (1989).
Parrillo et al, "Pathogenetic mechanisms of septic shock" *N Engl J Med* 328:20 1471-1477 (1993).
Seckinger et al, "A human inhibitor of tumor necrosis factor alpha", *J Exp Med* 167(4):1511-1516 (1988).
Tracey et al, "Shock and tissue injury Induced by recombinant human cachectin", *Science* 234(4775):470-474.
Tracey et al, "Anti-cachectin/TNF monoclonal antibodies prevent septic shock during lethal bacteraemia.", *Nature* 330(6149):662-664 (1987).
Unglaub et al, "Downregulation of tumor necrosis factor (TNF) sensitivity via modulation of TNF binding capacity by protein kinase C activators", *J Exp Med* 166(6):1788-1797 (1987).
Wallach D, "Cytotoxins (tumour necrosis factor, lymphotoxin and others): molecular and functional characteristics and interactions with interferons", *interferon* 7:89-124 (1986).

* cited by examiner

*Primary Examiner* — Ronald Schwadron
(74) *Attorney, Agent, or Firm* — Browdy and Neimark, PLLC

(57) ABSTRACT

An isolated DNA molecule has the sequence of encoding a fragment of encoding Tumor Necrosis Factor (TNF) Binding Protein II. It has a length sufficient to serve as an immunogen for raising antibodies against a polypeptide that is a fragment of TNF Binding Protein II. The DNA may be used to produce replicable expression vehicles and prokaryotic or eukaryotic expression host cells. Such host cells may be used to produce polypeptides encoded by such DNA molecules.

4 Claims, 8 Drawing Sheets

Sequence of TBPII peptides (tryptic digest purified on a C₁₈ column)

| | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| fraction 44[1] | Tyr | Tyr | Asp | Gln | Thr | Ala | Gln | Met | Cys | Cys | | | | | | | | | |
| fraction 50[1] | Leu | Arg | Val | Tyr | Tyr | Asp | Ala | Thr | Ala | Gln | Met | Cys | Cys | | | | | | |
| fraction 53[2] | Val | Ala | Phe | Thr | Pro | Tyr | Ala | Pro | Glu | Pro | Gly | Ser | Thr | Cys | Arg | | | | |
| fraction 53' | Cys | Arg | Pro | Gly | Phe | Gly | Val | Ala | Arg | | | | | | | | | | |
| fraction 60 | Ile | Cys | Thr | Cys | Arg | Pro | Gly | Trp | Tyr | Cys | Ala | Pro | Leu | | | | | | |
| fraction 84: | Thr | Ser | Asp | Thr | Val | Cys | Asp | Ser | Cys | Glu | Asp | Ser | Thr | Tyr | Thr | Gln | Leu | Trp | Asn |

[1] the sequences of the peptide in fraction 44 fully overlaps with the sequence of the peptide in fraction 50 both sequences represent the extension of the N-terminal sequence described for the intact TBP II

[2] The sequence of the peptide found in fraction 53 fully overlaps with the N-terminal sequence described for the intact TBP II

FIGURE 3

FIGURE_5

ISOLATED CDNA ENCODING TUMOR NECROSIS FACTOR BINDING PROTEIN II, ITS PURIFICATION, AND VECTORS, HOSTS AND PROCESSES USING SUCH CDNA

CROSS-REFERENCE TO RELATED APPLICATIONS

The present application is a continuation of U.S. application Ser. No. 08/485,129, filed Jun. 7, 1995, now abandoned which is a divisional of U.S. application Ser. No. 07/930,443, filed Aug. 19, 1992, which is a continuation of U.S. application Ser. No. 07/524,263, filed May 16, 1990, now abandoned.

FIELD OF THE INVENTION

This invention relates to a substantially purified Tumor Necrosis Factor (TNF) Binding Protein II (hereinafter TBP-II), salts, functional derivatives, precursors and active fractions thereof and mixtures of any of the foregoing, having the ability to inhibit the cytotoxic effect of TNF and/or to maintain prolonged beneficial effects of TNF. It also relates to a process for the purification of said TBP-II, to its cloning and its production by recombinant DNA techniques. The invention relates also to antibodies against TBP-II and to F(ab) fragments thereof. It further relates to pharmaceutical compositions comprising TBP-II, salts, functional derivatives, precursors, active fractions thereof and/or mixtures of any of the foregoing to antagonize the deleterious effects of TNF and/or to maintain its prolonged beneficial effects, and to the use of the antibodies in diagnostic assays or as agents for either inhibiting or mimicking the effects of TNF on cells.

BACKGROUND OF THE INVENTION

Tumor Necrosis Factor (TNF-α) and Lymphotoxin (TNF-β) (hereinafter, TNF refers to both TNF-α and TNF-β) are cytokines which have many effects on cells (Wallach, D. (1986) in: Interferon 7 (Ion Gresser, Ed.), pp. 90-124, Academic Press, London, and Beutler, B. and Cersmi, A. (1987) New England J. Med. 316:379-385). Both TNF-α and TNF-β initiate their effects by binding to specific cell surface receptors. Some of the effects are likely to be beneficial to the organism: they may destroy, for example, tumor cells or virus infected cells and augment antibacterial activities of granulocytes. In this way, TNF contributes to the defense of the organism against infectious agents and to recovery from injury. But, quite clearly, both TNF-α and TNF-β have also effects which can be extensively deleterious. There is evidence that over-production of TNF-α can play a major pathogenic role in several diseases. Thus, effects of TNF-α, primarily on the vasculature, are now known to be a major cause for symptoms of septic shock (Tracey, K. J. et al. (1986) Science 234:470-474). In some diseases, TNF may cause excessive loss of weight (cachexia) by suppressing activities of adipocytes and by causing anorexia and TNF-α was thus called cachectin. It was also described as a mediator of the damage to tissues in rheumatic diseases (Beutler, op. cit.) and as a major mediator of the damage observed in graft-versus-host reactions.

There is therefore a necessity in finding out ways to eliminate or antagonize endogenously formed or exogenously administered TNF. One attempt in this direction was the isolation from human urine of a first TNF Binding Protein called TBP-I and shown to be able to antagonize the effects of TNF. This antagonism was determined both by measuring reduction of the cytotoxic activity of TNF, as well as by measuring interference of TNF binding to its receptors.

The protein TBP-I was first described in our U.S. patent application Ser. No. 07/243,092 filed on Sep. 12, 1988, (now abandoned in favor of a continuation that issued as U.S. Pat. No. 5,595,953), in which was disclosed a process for its purification to homogeneity from human urine by chromatography on CM-SEPHAROSE followed by high performance liquid chromatography (HPLC) on MONO Q and MONO S columns and reversed-phase HPLC. The homogeneous TBP-I thus obtained had an apparent molecular weight of about 27,000 in sodium dodecyl sulfate (SDS)-polyacrylamide gel electrophoresis (PAGE) under both reducing and non-reducing conditions. Homogeneity of the purified protein was confirmed by microsequence analysis which revealed a single N-terminal sequence: Asp-Ser-Val-Cys-Pro-(SEQ ID NO: 1).

TBP-I was shown to protect cells from TNF toxicity at concentrations of a few nanograms per ml and to interfere with the binding of both TNF-α and TNF-β to cells, when applied simultaneously with these cytokines. Further examination of the mechanism by which TBP-I functions revealed that TBP-I does not interact with the target cell, but rather blocks the function of TNF by binding TNF specifically, thus competing for TNF with the TNF receptor.

As a result of this finding, we attempted an alternative approach for the purification of TBP-I, whereby urinary proteins or fractions thereof were applied on a column of immobilized TNF and, after removal of unbound proteins, the proteins which bound to the column were eluted, in bioactive form, by a decrease of the pH. In SDS PAGE analysis, most of the protein in the eluate migrated as a single broad band with apparent molecular size of 30,000±2,000.

When applied to further fractionation by reversed-phase HPLC, the proteins eluting from the TNF col showed the presence of two active components: one, TBP-I, eluting as expected at 27% acetonitrile and, in addition, a second TNF-binding protein, eluting at a somewhat higher acetonitrile concentration (31%). This TNF-binding protein is new and is herein called TBP-II. Both proteins provide protection against the in vitro cytocidal effect of TNF and both bind TNF-β less effectively than TNF-α. Although in SDS PAGE analysis the two proteins, TBP-I and TBP-II, appeared to have a very similar molecular size, they could clearly be distinguished from each other by lack of immunological cross reactivity, differing N-terminal amino acid sequences and differing amino acid composition.

SUMMARY OF THE INVENTION

The present invention provides substantially purified TNF-Binding Protein, herein designated TBP-II, salts, functional derivatives, precursors and active fractions thereof and mixtures of any of the foregoing, which binds TNF specifically and can antagonize the deleterious effects of TNF and/or maintain its prolonged beneficial effects. The antagonism to TNF is determined by selectively measuring reduction of cytotoxic activity of TNF, but not of other compounds having some activities similar to TNF, such as human interleukin-1 (IL-1).

The invention is directed to said TBP-II in substantially purified form, being free of proteinaceous impurities and moving as a single peak on reversed HPLC.

The invention also relates to a process for the purification of TBP-II from human fluids, such as urine.

Another object of the invention is the production of TBP-II by recombinant DNA techniques, including the preparation of DNA sequences coding for TBP-II or for a protein substantially homologous therewith, the construction of expression vehicles comprising them and of host cells transformed therewith, and the culture of said transformant cells in a suitable culture medium in order to produce recombinant TBP-II or a protein substantially homologous therewith.

A further object of the invention is to provide antibodies specific for TBP-II and F(ab) fragments thereof, which may be used in diagnostics as well as in pharmaceuticals both for inhibiting toxic effects of TNF and for mimicking TNF beneficial effects on cells.

The TBP-II of the invention and its salts, functional derivatives, precursors and active fractions thereof, and mixtures of any of the foregoing, are for use as active ingredients of pharmaceutical compositions and in medical treatment to protect mammals against the deleterious effects of TNF and/or to maintain its prolonged beneficial effects, when used together with TNF.

BRIEF DESCRIPTION OF THE FIGURES

FIG. 3 depicts the sequences of several tryptic peptides of TBP-II. Fraction 44 is residues 21-30 of SEQ ID NO:2. Fraction 50 is SEQ ID NO:3. Fraction 53 (first) is residues 3-17 of SEQ ID NO:2. Fraction 53 (second) is SEQ ID NO:4. Fraction 60 is SEQ ID NO:5. Fraction 84 is SEQ ID NO:6.

DETAILED DESCRIPTION OF THE INVENTION

Figure 1:
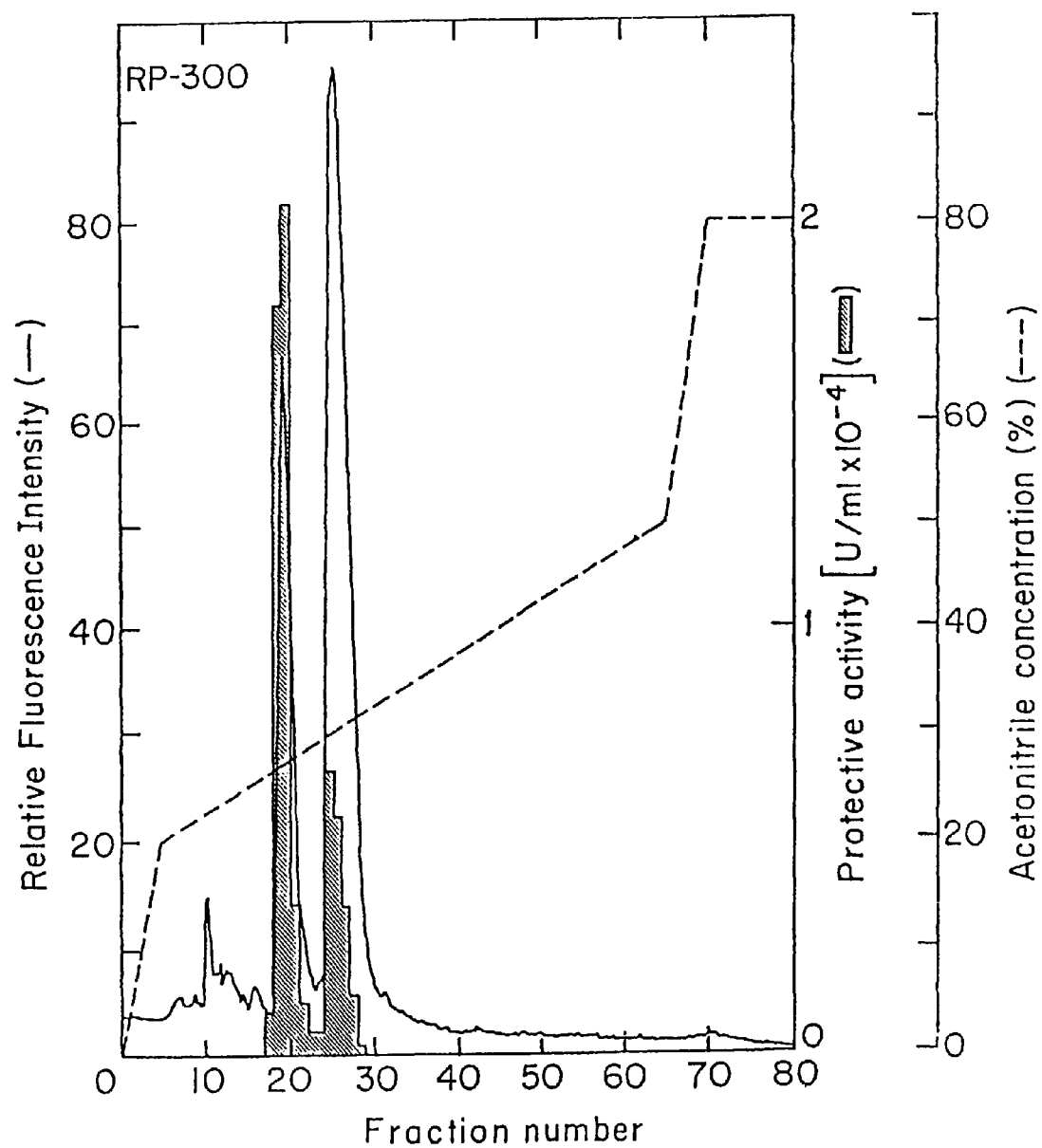
FIG. 1 shows the elusion pattern of urinary TNF binding proteins on a reversed-phase HPLC column.

The present invention provides TNF Binding Protein TBP-II, salts, functional derivatives, precursors and active fractions thereof, and mixtures of any of the foregoing, which selectively inhibit the cytotoxic effect of TNF and/or maintain its prolonged beneficial effects.

It was found according to the present invention that TBP-II is able to inhibit the cytotoxic activity of TNF and thus the inhibition of the cytotoxic effects of TNF by TBP-II is encompassed by the present invention. It was further found that TBP-II has an additional role as a specific carrier which binds TNF and maintains its prolonged beneficial effects. Thus, the complex TBP-II bound-TNF may act as a reservoir which provides a sustained release of active TNF to target cells. This aspect is also encompassed by the present invention, including the use of TBP-II in low amounts together with TNF, to promote prolonged beneficial effects of TNF, such as antitumor, antiviral, antibacterial, antiparasitic, or fibroblast growth stimulating activity. In this case, the mixture may have several clinical applications, such as promotion of wound healing.

The TBP-II of the invention was isolated from human urine. The substantially purified protein, which is substantially free of proteinaceous impurities, has a molecular weight of about 30 kDa when analyzed by SDS PAGE under reducing conditions and it moves as a single peak on reversed-phase HPLC. Its activity is determined by its ability to inhibit the cytotoxic effect of TNF-α on murine A9 cells.

TBP-II is further characterized by the following sequence obtained by N-terminal sequence analysis of the protein:
Ala-Gln-Val-Ala-Phe-Thr-Pro-Tyr-Ala-Pro-Glu-Pro-Gly-Ser-Thr-Cys-Arg-Leu-ArgGlu-Tyr-Tyr-Asp-Gln-Thr-Ala-Gln-Met-Cys-Cys (SEQ ID NO: 2)

In fact, a heterogeneity of N-terminal sequences could be observed in the sample of TBP-II and in all experiments truncated forms of this sequence could be discerned. The amounts of the different truncated sequences and the ratio to each other varied from batch to batch. Thus together with the above sequence, one could discern a sequence shorter by five amino acids:
Thr-Pro-Tyr-Ala-Pro-Glu-Pro-Gly-Ser-Thr . . . (residues 6-15 of SEQ ID NO: 2)

and a sequence which lacked just four of the terminal amino acids:
Phe-Thr-Pro-Tyr-Ala-Pro-Glu-Pro-Gly-Ser-Thr . . . (residues 5-15 of SEQ ID NO: 2)

The present invention encompasses a protein comprising the above sequence, herein referred to as TBP-II, as well as any other polypeptide in which one or more amino acids in the structure of natural TBP-II are deleted or replaced with other amino acids, or one or more amino acids are added thereto, as long as they have human TBP-II activity.

This invention also relates to a process for isolating TBP-II from a human fluid, e.g., urine, and its purification. In one preferred embodiment, the substantially purified protein of the invention is produced by a process which comprises:
(a) recovering the crude protein fraction from a dialyzed concentrate of human urine of healthy patients;
(b) subjecting said crude protein fraction of step (a) to affinity purification on a column of immobilized TNF;
(c) applying said affinity purified active TNF Binding Proteins from step (b) to reversed-phase HPLC to obtain substantially purified active fractions of the TNF Binding Proteins, defined by their ability to inhibit the cytotoxic effect of TNF;
(d) separating the substantially purified proteins of step (c) having a molecular weight of about 30 kDa on SDS PAGE under reducing conditions, moving as a single peak on reversed-phase HPLC and having the ability to inhibit the cytotoxic effect of TNF; and
(e) recovering the fractions eluting at 31: acetonitrile and containing substantially purified TBP-II.

The invention further relates to the preparation of TBP-II by genetic engineering techniques and encompasses all the tools used in these techniques. Thus, the invention concerns DNA molecules comprising the nucleotide sequence coding for TBP-II or for a protein substantially homologous therewith. These DNA molecules may be genomic DNA, CDNA, synthetic DNA and combinations thereof.

The cloning of TBP-II may be carried out by different techniques. According to one approach, specific antibodies (polyclonal or monoclonal) to TBP-II are produced and used to search for cells producing TBP-II by immunofluorescence or by Western blot. Then, mRNA is extracted from these TBP-II producing cells and is converted to cDNA by contacting with reverse transcriptase for a time and under conditions suitable to form said cDNA. The cDNA is cloned in an expression vector such as lambda gT 11, and screened by the use of the antibodies. The lambda gT 11 expression vector can be used for insertion of DNA up to 7 kb in length at a unique EcoRI site 53 bases upstream from the β-galactosidase termination codon. Therefore, foreign sequences DNA may be inserted into this site and expressed under appropriate conditions as fusion proteins. The lambda gT 11 expression vector is particularly useful for the construction of cDNA libraries to be screened with antibody probes (Huynh, T. V. et al. in: David Glover (ed.), *DNA Cloning Techniques: A Practical Approach*, IRL Press, Oxford (1984) pp. 49-78).

Following another approach, a synthetic oligonucleotide or a mixture of synthetic oligonucleotides, whose sequence is derived from the amino acid sequence of a fragment of the protein, e.g., the N-terminal amino acid sequence, are produced and used as probes for cloning the cDNA or the genomic DNA coding for TBP-II. Suitable DNA preparations, such as human genomic DNA, are enzymatically cleaved by restriction enzymes, or randomly sheared, and the fragments inserted into appropriate recombinant vectors to form a gene library. Such vectors can then be screened with synthetic oligonucleotide probes in order to identify a sequence coding for TBP-II.

Alternatively, the mRNA is isolated from cells which express TBP-II and is converted, after purification, to cDNA as described above. The cDNA is converted to double-stranded cDNA by known techniques, is cloned and the resulting clones are screened with an appropriate probe for cDNA coding for the desired sequences. Once the desired clone is isolated, the cDNA is manipulated in substantially the same manner as the genomic DNA. However, with cDNA there will be no introns or intervening sequences.

The invention also relates to synthetic oligonucleotides to be used as probes to the DNA coding for TBP-II. They are synthesized by known methods on the basis of the amino acid sequence of fragments of TBP-II. For this purpose, it is possible either to perform sequence analysis of the intact TBP-II or to obtain peptide fragments thereof and to characterize their amino acid sequence. The peptide fragments are obtained by subjecting purified protein preparations to fragmentation, e.g., by digestion with proteases such as trypsin, chymotrypsin or papain by methods well known in the art (Oike, Y. et al. (1982) *J. Biol. Chem.* 257:9751-9758), they are separated by reverse phase HPLC and sequenced by automatic amino acid sequencing techniques.

Once one or more suitable peptide fragments have been sequenced or a partial sequence of the protein is determined, the DNA sequences capable of encoding them are examined. Due to the degeneration of the genetic code, more than one codon may be used to encode a particular amino acid and one or more different oligonucleotides can be produced, each of which would be capable of encoding the TNF Inhibitory Protein peptide fragments (Watson, J.D., in: *Molecular Biology of the Gene*, 3rd ed., W.A. Benjamin, Inc. Menlo Park, CA (1977), pp. 356-357). Thus, for example, the genetic code provides that the generic DNA sequence that comprises all of the codons that will encode the amino acid sequence of residues 6-15 of SEQ ID NO:2 is: ACN-CCN-TAY-GCN-CCN-GAR-CCN-GGN-(TCN or AGY)- ACN (SEQ ID NO:7), where N is A or G or C or T; Y is T or C; and R is G or A.

However, only one member of the set contains the nucleotide sequence that is identical to the nucleotide sequence of the gene. Its presence within the set and its capability to hybridize to DNA even in the presence of the other members of the set, makes it possible to employ the unfractionated set of oligonucleotides in the same manner in which one would employ a single oligonucleotide to clone the gene that encodes the peptide. The use of such oligonucleotide or set of oligonucleotides containing the theoretical "most probable" sequence capable of encoding the TBP-II gene fragments (following the "codon usage rules" disclosed by Lathe, R., et al. (1985) *J. Molec. Biol.* 183:1-12) permits to identify the sequence of a complementary oligonucleotide or set of oligonucleotides which is capable of hybridizing to the "most probable" sequence encoding the TBP-II or at least a portion thereof, or a set of such sequences.

This oligonucleotide containing such a complementary sequence is then synthesized and employed as a probe to identify and isolate a DNA molecule coding for the TBP-II of the invention from a DNA library (Maniatis, T. et al. *Molecular Cloning: A Laboratory Manual*, Cold Spring |Harbor Press, Cold Spring Harbor, N.Y. (1982)).

In one of the embodiments, the isolation of the gene of TBP-II is done by colony hybridization techniques under stringent conditions. Procedures for hybridization of nucleic acids are common knowledge and are disclosed, for example, in Maniatis, T., *Molecular Cloning: A Laboratory Manual*, op. cit. and in Haymes, B. T., et al., *Nucleic Acid Hybridization: A Practical Approach*, IRL Press, Oxford, England (1985). By hybridization with the above nucleotide or set of oligonucleotides probes, it is possible to identify in a cDNA or genomic library, the DNA sequences capable of such hybridization, and they are then analyzed to determine to what extent they contain encoding sequences for the TBP-II of the invention.

The DNA of positive clones is then inserted into appropriately constructed expression vectors by techniques well known in the art (see Maniatis et al., op cit.). Double-stranded cDNA is linked to plasmid vectors by homopolymeric tailing or by restriction linking involving the use of synthetic DNA linkers or blunt-ended ligation techniques. DNA ligases are used to ligate the DNA molecules and undesirable joining is avoided by treatment with alkaline phosphatase.

For expression of the desired protein, the expression vector should comprise also specific nucleotide sequences containing transcriptional and translational regulatory information linked to the DNA coding for the desired protein in such a way as to permit gene expression and production of the protein. First, in order for the gene to be transcribed, it must be preceded by a promoter recognizable by RNA polymerase, to which the polymerase binds and thus initiates the transcription process. There are a variety of such promoters in use, which work with different efficiencies (strong and weak promoters) and are different for prokaryotic and eukaryotic cells. High levels of gene expression in prokaryotic cells are achieved by using also ribosome-binding sites, such as the Shine-Dalgarno sequence (SD sequence). For eukaryotic hosts, different transcriptional and translational regulatory sequences may be employed, depending on the nature of the host. They may be derived from viral sources, such as adenovirus, bovine papilloma virus, Simian virus, or the like, where the regulatory signals are associated with a particular gene which has a high level of expression. Examples are the TK promoter of Herpes virus, the SV40 early promoter, the yeast gal4 gene promoter, etc. Transcriptional initiation regulatory signals may be selected which allow for repression and activation, so that expression of the genes can be modulated.

The DNA molecule comprising the nucleotide sequence coding for a protein comprising the amino acid sequence of the TBP-II of the invention preceded by a nucleotide sequence of a signal peptide and the operably linked transcriptional and translational regulatory signals is inserted into a vector which is capable of integrating the desired gene sequences into the host cell chromosome. The cells which have stably integrated the introduced DNA into their chromosomes can be selected by also introducing one or more markers which allow for selection of host cells which contain the expression vector.

In a preferred embodiment, the introduced DNA molecule will be incorporated into a plasmid or viral vector capable of autonomous replication in the recipient host. Prokaryotic and eukaryotic plasmids are well known from the literature. Factors of importance in selecting a particular plasmid or viral vector include the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. Host cells to be used in this invention may be either prokaryotic or eukaryotic. Preferred prokaryotic hosts include bacteria such as E. coli, Bacillus, Streptomyces, Pseudomonas, Salmonella, Serratia, etc. The most preferred prokaryotic host is E. coli. Under such conditions, the protein will not be glycosylated. The prokaryotic host must be compatible with the replicon and control sequences in the expression plasmid. Preferred eukaryotic hosts are mammalian cells, e.g., human, monkey, mouse and Chinese hamster ovary (CHO) cells, because they provide post-translational modifications to protein molecules, including correct folding or glycosylation at correct sites. Also yeast cells can carry out post-translational peptide modifications, including glycosylation.

After the introduction of the vector, the host cells are grown in a selective medium, which selects for the growth of vector-containing cells. Expression of the cloned gene sequence(s) results in the production of the desired TBP-II or a fragment thereof. The expressed protein is then isolated and purified in accordance with the purification method described in the present application or by any other conventional procedure involving extraction, precipitation, chromatography, electrophoresis, or the like.

A further purification procedure that may be used in preference for purifying the protein of the invention is affinity chromatography using anti-TBP-II monoclonal antibodies, which are produced and immobilized on a gel matrix contained within a column. Impure preparations containing the recombinant protein are passed through the column. The protein will be bound to the column by the specific antibody while the impurities will pass through. After washing, the protein is eluted from the gel by a change in pH or ionic strength.

As used herein the term "salts" refers to both salts of carboxyl groups and to acid addition salts of amino groups of the protein molecule formed by means known in the art. Salts of a carboxyl group include inorganic salts, for example, sodium, calcium, and salts with organic bases as those formed, for example, with amines, such as triethanolamine, arginine or lysine. Acid addition salts include, for example, salts with mineral acids and salts with organic acids.

"Functional derivatives" as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the protein and do not confer toxic properties on compositions containing it. These derivatives include aliphatic esters or amides of the carboxyl groups, and N-acyl derivatives of free amino groups or O-acyl derivatives of free hydroxyl groups formed with acyl moieties (e.g., alkanoyl or carbocyclic aroyl groups).

"Precursors" are compounds formed prior to, and converted into, TBP-II in the animal or human body. As "active fractions" of the substantially purified protein, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has the ability to inhibit the cytotoxic effect of TNF on cells and/or to maintain its prolonged beneficial effect.

The invention further relates to antibodies against TBP-II and to F(ab) fragments thereof, and to salts, functional derivatives and/or active fractions (as hereinbefore defined) thereof. These antibodies provide a new approach for the modulation of the TNF activity, and may be used both to inhibit and to mimic effects of TNF on specific subsets of cells, depending on the molecular form of the antibodies, specifically on their valence: monovalent forms of the antibodies (e.g., F(ab) fragments) being inhibitory and multivalent forms being able to mimic at least part of the effects of TNF. They are, thus, suitable as pharmaceutical agents both for mimicking and blocking TNF effects on cells.

The functional interaction of the antibodies of the present invention with TBP-II provides also a new diagnostic tool, based on immunoassays such as radioimmunoassay, ELISA, etc., for the detection of over- or under-production of TBP-II by cells in the body in certain disorders. Thus, the level of TBP-II in sera of patients with different types of cancer or suffering from autoimmune disorders, such as systemic lupus erythematosus (SLE), can be determined this way. In an inverse approach, antibodies against TBP-II, when produced endogenously in the body, will be measured with the use of purified TBP-II. Detecting such autoantibodies, when formed in certain autoimmune disorders, is of extreme importance, since their ability to mimic or inhibit the effects of TNF surely has a far-reaching bearing on the pathological syndromes of said disorders.

The antibodies may be either polyclonal or monoclonal. They may be raised in rabbits, mice or other animals or tissue cultured cells derived thereof or can be products of cells of human origin. They may also be produced by recombinant DNA technology either in a form identical to that of the native antibody or as chimeric molecules, constructed by recombination of antibody molecules of man and animal origins or in other forms chosen to make the antibodies most suitable for use in therapy.

For the preparation of the antibodies, either purified TBP-II or one or more synthetic peptides identical to the known sequence of a fragment thereof, e.g., to the N-terminal protein sequence, may be used to immunize animals. A further possibility is to fuse one of the possible nucleotide sequences coding for a fragment of TBP-II to the gene coding for Protein A, to express the fused Protein A-TBP-II gene in E. coli, to purify the fused protein by G affinity chromatography on IgG SEPHAROSE column and then to use it to immunize animals.

The monoclonal antibodies of the present invention are prepared using conventional hybridoma technique (Kohler et al. (1975) Nature 256:495; Rohler et al. (1976) Eur. J. Immunol. 6:511). After immunization, spleen cells alone or together with lymph node cells of the immunized animals are isolated and fused with a suitable myeloma cell line. After fusion, the resulting hybridoma cells are selectively maintained in HAT medium and then cloned. The hybridoma cells obtained through such a selection are then assayed to identify clones which secrete antibodies capable of binding TBP-II. After identification, the desired clones are grown in bulk, either in suspension culture or in ascitic fluid, by injecting the cells into the peritoneum of suitable host mice. The monoclonal antibodies produced by the hybridomas are then isolated and purified.

As mentioned before, the monoclonal antibodies may also be immobilized and used for the purification of the TBP-II in affinity purification procedure using an immunoadsorbent column.

The TBP-II and salts, functional derivatives, precursors and active fractions thereof and mixtures of any of the foregoing, are indicated for antagonizing the deleterious effects of TNF in mammals, i.e., for treating conditions wherein excess of TNF is formed endogenously or is exogenously administered. They are also indicated, in low amounts and in mixture with TNF, as carriers for prolonging beneficial effects of TNF.

The present invention further relates to pharmaceutical compositions comprising a pharmaceutically acceptable carrier and the TBP-II of the invention or its salts, functional derivatives, precursors or active fractions thereof or mixtures of any of the foregoing, as active ingredient. These compositions may be used in any condition where there is an overproduction of endogenous TNF, such as in cases of septic shock, cachexia, graft-versus host reactions, autoimmune diseases like rheumatoid arthritis, etc. The way of administration can be via any of the accepted modes of administration for similar agents and will depend on the condition to be treated, e.g., intravenously in case of septic shock or local injection in case of rheumatoid arthritis (for example, into the knee), or continuously by infusion, etc. The compositions may also be used in cases of TNF intoxication caused by exogenous administration of excessive amounts (overdoses) of TNF. The compositions may comprise also TNF, in which case it will release TNF in a controlled manner for a prolonged time.

The pharmaceutical compositions of the invention are prepared for administration by mixing the protein or its derivatives with physiologically acceptable carriers, stabilizers and excipients, and prepared in dosage form, e.g., by lyophilization in dosage vials. The amount of active compound to be administered will depend on the route of administration, the disease to be treated and the condition of the patient. Local injection in case of inflammatory conditions of rheumatoid arthritis will require less TBP-IL on a body weight basis than will intravenous infusion in case of septic shock.

The invention will now be illustrated by the following non-limiting examples:

EXAMPLE 1

Purification of TBP-II 1.1 Preparation of the Urine Concentrate

A pool of 200 l urine from healthy male donors or from healthy postmenopausal women was subjected to microfiltration on a PELLICON membrane with a pore size of 0.45 μm. The filtrate was concentrated by ultrafiltration using a PELLICON membrane with a molecular weight cut-off of 10 kDa to a final volume of 500 ml. The concentrate was dialyzed against phosphate buffered saline containing 1 mM benzamidine and 0.1% sodium azide.

1.2 Affinity Purification of TBP-I and TBP-II on a Column of Immobilized TNF

Recombinant TNF-α was brought to a concentration of 7.2 mg/ml, then equilibrated with PBS containing 0.02% sodium azide and coupled to AFFIGEL 10 (3.6 mg to 0.5 ml beads of cross-linked agarose gel matrix with N-hydroxysuccinimide functional group with specificity for $-NH_2$). A sample of 250 ml of the concentrate of urinary proteins of step 1.1 was applied to a column constructed from the beads of the immobilized TNF at a flow rate of 0.2-0.3 ml/minute at 4° C. Unbound proteins were removed by washing with PBS and the bound proteins were then eluted by applying a solution of 25 mM citric acid, 100 mM NaCl and 0.02% sodium azide, at pH 2.5. The specific bioactivity (inhibition of TNF toxicity) of the eluted proteins was about 20,000-fold higher than that of the crude urinary proteins (Table I). In SDS PAGE analysis, most of the protein in the eluate migrated as a single broad band with apparent molecular size of about 30,000±2,000.

1.3 Reversed-Phase High Pressure Liquid Chromatography (HPLC)

Further fractionation of the affinity purified proteins of step 1.2 was by reversed-phase HPLC on an AQUAPORE RP300 reversed-phase chromatography column (4.6×30 mm, Brownlee Labs), first pre-equilibrated and then washed with 0.3% aqueous trifluoroacetic acid (TFA) (BUFFER F) until a stable baseline was obtained by the fluorescamine detection system. Pooled active fractions eluted from the affinity TNF column of step 1.2 were applied on the column, elusion was performed at a flow rate of 0 5 ml/minute with linear gradients of acetonitrile in BUFFER F (0-20% for 5 minutes, followed by 20-50% for 60 minutes and finally 50-80% for 5 minutes), and then the column was washed for 15 minutes with 80% acetonitrile. Fractions of 0.5 ml were collected and examined for protein content (--) and for bioactivity (■), as shown in FIG. 1 (---- stands for elution with gradient of acetonitrile in BUFFER F).

The bioactivity was measured by the same bioassay developed for TBP-I. It is based on the cytotoxic effect of TNF on cycloheximide (CHI)-sensitized cells and its quantitation by the neutral-red uptake method, as described in Wallach, D. (1984) *J. Immunol.* 132:2464-2469. It is used in the present invention for monitoring the activity of TBP-II during purification.

Samples to be tested for the presence of the protein were diluted two-fold serially, at 4° C., in Dulbecco's Modified Eagle's Minimal Essential Medium (DMEM), and equal volumes of the same medium containing 40 U/ml TNF-α and 400 μg/ml cycloheximide (CHI) is added thereto. The final concentration of TNF-α on the cells was 5 U/ml and of CHI was 50 μg/ml.

Murine A9 cells were seeded in 96-well flat-bottom microtiter plates ($1.5 \times 10^4$ cells/ well) with 100 μl DMEM-CS (DMEM containing 5% fetal calf serum and 5% calf serum).

100 μl aliquots of the serially diluted protein TNF-α-CHI mixtures were applied to each well and the cells were further incubated for 14 hours.

Viability of the cells was determined by incubation with neutral red for 2 hours, washing away excess dye, extracting the neutral red that was taken up by the cells with Sorenson's citrate buffer-ethanol mixture, and quantitating it colorimetrically at 570 nm with a Microelisa Auto-reader.

1 U/ml of TNF inhibitor activity was defined as the dilution factor giving a statistically significant protection from TNF killing (p<0.05).

TABLE I

Purification of TBP-I and TBP-II

| Purification Step | Protein mg | Protective Activity Units | % | Specific Activity units*/mg | Purification fold |
|---|---|---|---|---|---|
| Crude urinary proteins | 9,400 | 117,200 | 100 | 12.4 | |
| Affinity purification | | | | | |
| Flow through | 9,300 | Below Detection | | | |
| Eluted proteins | 0.36 | 98,600 | 84.2 | 273,800 | 22,000 |
| Reversed-phase HPLC | | | | | |
| Total | 0.217 | 31,200 | 26.6 | 143,400 | 11,600 |
| TBP-I | 0.070 | 22,300 | 19.0 | 318,600 | |
| TBP-II | 0.147 | 8,900 | 7.6 | 60,700 | |

*A unit of protective activity was defined as the amount of TNF-binding proteins in whose presence the number of cells remaining viable under the conditions of the assay for the protective effect of the proteins against TNF cytotoxicity, was doubled.

As shown in FIG. 1, the active proteins were found to elute from the HPLC column as two distinct protein peaks, in fractions corresponding to about 27% acetonitrile (TBP-I) and about 31% acetonitrile (TBP-II). Both proteins had a protective effect against TNF cytotoxicity, though the specific activity of TBP-II was lower than that of TBP-I (Table I).

The inhibitory effect of TBP-II on the binding of radiolabeled TNF to cells was performed as described by Olsson, I. et al (1989) *Eur. J. Hematol.* 42:270-275. As with TBP-I, it was observed that TBP-II decreases the $^{125}$I-TNF-α binding to the cells only when $^{125}$I-TNF-α and TBP-II are applied together on cells and not when TBP-II is first applied on cells and then removed prior to the application of TNF-α. This indicates that the interference with TNF-α binding to cells is not due to an effect of TBP-II on the cells, but it rather reflects some kind of interaction between TBP-II and TNF-α.

The binding activities of TBP-I and TBP-II were examined in a solid phase assay with the use of radiolabeled preparations of the proteins. Both were found to bind TNF-α and this binding could be competed with excess TNF-α and, at a lower effectivity, also with TNF-α. It could not be competed, though, with several other cytokines examined (IL-1, IL-6, IFN-gamma, Table II).

TABLE II

Binding of TBP-I and TBP-II to TNF-α and the Effect of Competitive Cytokines

| Proteins Applied* for Competition for TBP Binding | $^{125}$I TBP-I (bound CPM) | $^{125}$I TBP-II (bound CPM) |
|---|---|---|
| — | 27700 (±2000) | 17634 (±1230) |
| huTNF-α | 1050 (±140) | 2400 (±174) |
| huTNF-β | 21000 (±850) | 6250 (±230) |
| IL-1α | 28100 (±460) | 17840 (±890) |
| IL-6 | 27050 (±570) | 18570 (±1120) |
| IFN-gamma | 28050 (±1050) | 18470 (±1430) |
| TBP-I | 1900 (±170) | 2240 (±160) |
| TBP-II | N.D. | 2005 (±150) |

*All proteins were applied at a concentration of 10 µg/ml.

1.4 SDS-PAGE

Figure 2:
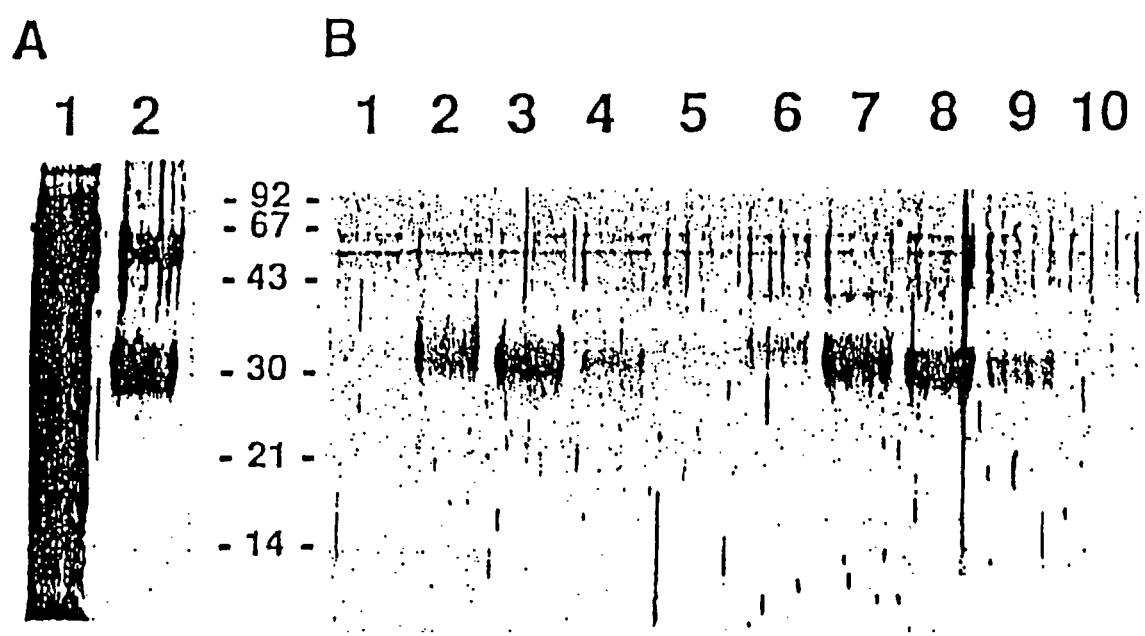
FIG. 2 shows SDS-PAGE analysis of the crude and purified preparations of TBP-I and TBP-II.

In order to monitor the result of the purification, sodium dodecyl sulfate polyacrylamide gel electrophoresis (SDS-PAGE) was performed according to the method of Laemmli U.K. et al. (1970) *Nature* 227:680. In FIG. 2A, analysis under reducing conditions of the affinity purification step is shown: lane 1—unfractionated urinary proteins; lane 2—proteins eluted from the TNF column by the low pH buffer. In FIG. 2B, analysis under reducing conditions of active fractions eluting from the reversed-phase HPLC, is shown. Samples were mixed with 3× concentrated sample buffer containing 6% SDS (w/v) and 15% v/v β-mercaptoethanol and loaded on a 12% acrylamide gel (lanes 1-4: TBP-I; Lanes 5-9: TBP-II). As a reference for molecular weight, a mixture of molecular weight markers (a lactalbumin 14.4 kDa, soya bean trypsin inhibitor 20.1 kDa, carbonic anhydrase 30 kDa, ovalbumin 43 kDa, bovine serum albumin 67 kDa, and phosphorylase b. 94 kDa) was used. A blank with sample buffer was run on lane 10. The gel was run at 160 volt and the protein bands were visualized by silver staining (Oakley, B. R. et al. *Anal. Biochem.* 105:361).

1.5 N-Terminal Sequence Analysis

Samples of the substantially purified TBP-II of the invention (1-5 µg, 50-200 pmol each) were applied to pretreated, biobrene-coated glass-fiber discs. The dried discs were subjected to repetitive cycles of Edman degradation in an automated pulsed liquid gas phase protein microsequencer (Model 475) with an on-line HPLC PTH-amino acid analyzer (Model 120) and a data acquisition and processing unit Model 900, (all from Applied Biosystems Inc., Foster City, Calif., U.S.A.). The computer-derived sequence was compared with the raw data and was corrected when necessary. Altogether three separate analyses were performed in order to confirm the sequence data. The initial yield was over 40%, indicating that the major protein in the preparation (the 30 kDa band) is related to the resulting sequence.

N-terminal sequence analysis of the protein of fraction 27 (FIG. 1) gave the following sequence:

Val-Ala-Phe-Thr-Pro-Tyr-Ala-Pro-Glu-Pro-Gly-Ser-Thr-Cys-Arg-Leu-Arg-Glu-Tyr-Tyr-Asp (residues 3-23 of SEQ ID NO: 2)

accompanied by higher amounts of a sequence shorter by 3 amino acids:

Thr-Pro-Tyr-Ala-Pro-Glu-Pro-Gly-Ser-Thr (residues 6-15 of SEQ ID NO: 2)

and by even higher amounts of a sequence lacking two terminal amino acids:

Phe-Thr-Pro-Tyr-Ala-Pro-Glu-Pro-Gly-Ser-Thr (residues 5-15 of SEQ ID NO: 2)

On the other hand, in fraction 28, the sequence Val-Ala-Phe-Thr-Pro- . . . (residues 3-7 of SEQ ID NO: 2)was the major one and, in addition, one could discern at lower amounts the shorter sequence Phe-Thr-Pro- . . . , and at even lower amounts, the sequence Thr-Pro- . . .

The least truncated sequence of the protein obtained from different batches of purified TBP-II was as follows:

Ala-Gln-Val-Ala-Phe-Thr-Pro-Tyr-Ala-Pro-Glu-Pro-Gly-Ser-Thr-Cys-Arg-Leu-Arg-Glu-Tyr-Tyr-Asp-Gln-Thr-Ala-Gln-Met-Cys-Cys (SEQ ID NO: 2).

EXAMPLE 2

Preparation of Tryptic Peptides of TBP-II

Purified TBP-II (180 µg) was reduced and alkylated as described by Andrews, P. C. and Dixon, J. E., (1987) *Anal. Biochem.* 161:524-528. It was then applied again on an AQUAPORE RP300 column (see example 1.3) in order to remove residues of the reduction—alkylation reagents. The purified TBP-II was then fragmented by digestion overnight with trypsin (substrate/enzyme ratio of 20:1). at pH 8.0. The peptides obtained were purified by reversed-phase HPLC on a C-18 SYNCHROPAK® RP-P column of monomerically bonded C-18 phase on 6 μm, 300Å spheroidal silica. The sequences of six peptides comprised in fractions 44, 50, 53, 53', 60 and 84 were determined as in Example 1.5 and are depicted in FIG. 3.

EXAMPLE 3

Preparation of Polyclonal Antibodies Against TBP-II

For the immunization of rabbits, the animals were first injected subcutaneously with 20 μg of TBP-II as emulsion in complete Freund adjuvant. Three weeks later they were injected again, intramuscularly, as emulsion in incomplete Freund adjuvant and then twice again subcutaneously as solution in PBS, at one week intervals. The rabbits were bled 10 days after the last immunization.

For the purification of immunoglobulins from the rabbit serum, saturated ammonium sulfate was added to 10 ml serum to a final concentration of 50% saturation. After overnight incubation at 4° C., the immunoglobulins were precipitated by centrifugation. The pellet was washed twice with 50% ammonium sulfate, then solubilized in 10 mM sodium borate 0.02% sodium azide at pH 9. The solution was then dialyzed extensively against the borate-azide solution. It was then applied for chromatography on HPLC MONO-Q quaternary ammonium strong anion exchanger column, from which the proteins were eluted with a gradient of 0-500 mM NaCl in the above borate-azide solution. The immunoglobulins eluted at a salt concentration of approximately 70 mM NaCl.

The antiserum to TBP-II suppressed the binding of $^{125}$I-TNF to U-937 cells by about 50% at a dilution of 1:6400. Antiserum to TBP-I was raised in rabbits in the same conditions and the extent of the immunological cross-reactivity of both antisera were examined by Western blot analysis. It showed that TBP-I and TBP-II are immunologically distinct: each antiserum recognized significantly only that species of TBP against which it had been raised.

Figure 4:
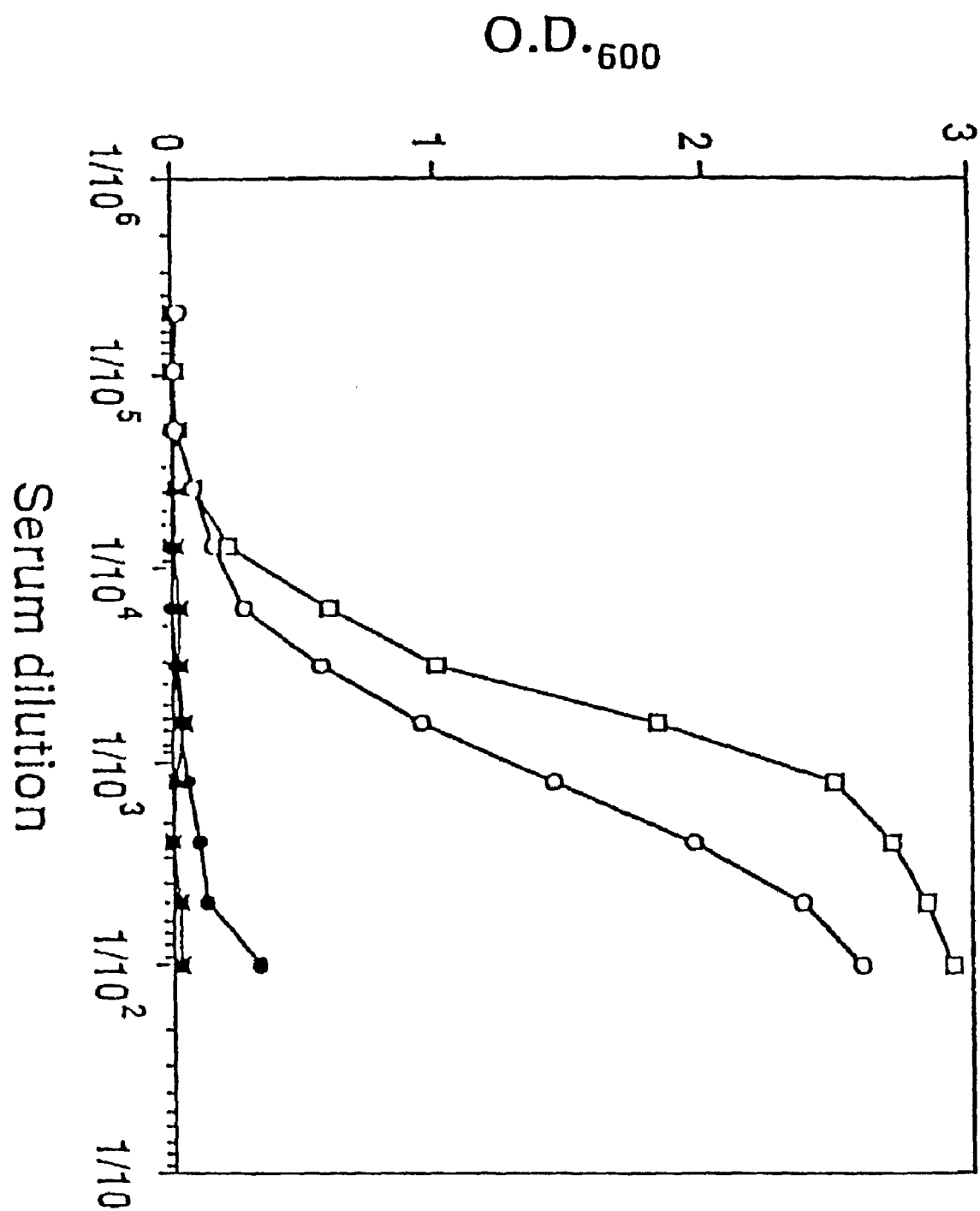
FIG. 4 shows ELISA for the binding of antisera against TBP-I and TBP-II for the two species of TBP.

Similarly, when examining the interaction of the antisera and the proteins in ELISA, the antiserum against TBP-I was found to reset with TBP-I at a dilution of up to 1:25,000, but did not react with TBP-II, not even at a dilution of 1:100. FIG. 4 shows the results of ELISA for the binding of antisera against TBP-I and TBP-II to the two species of TBP. The binding of (□) antiserum against TBP-I to TBP-I, (■) antiserum against TBP-I to TBP-II, (●) antiserum against TBP-II to TBP-I, and (○) antiserum against TBP-II to TBP-II, is presented in terms of the absorbance of the color product in the horseradish peroxidase assay. The readings in a control test at which the antibodies were applied on wells coated with BSA were subtracted. (The slight binding of the antiserum against TBP-II to TBP-I, observed in FIG. 2, could be shown to be due to contamination of the antiserum with antibodies to TBP-I, at low amounts, due to the presence of some TBP-I in the preparation of TBP-II used for immunization).

EXAMPLE 4

Effects of the Polyclonal Antibodies on Binding of TNF to Cells

The antisera to TBP-I and TBP-II were diluted in Dulbecco's balanced salt solution (PBS+) containing 0.5% BSA and 0.1% sodium azide (PBS/BSA) and then either directly or, in competition experiments, after incubation with a sample of TBP, applied for 2 hours on the tested cells of the HeLa, MCF7, K562 and U937 cell lines. The cells were then rinsed and tested for binding of TNF.

Figure 5:
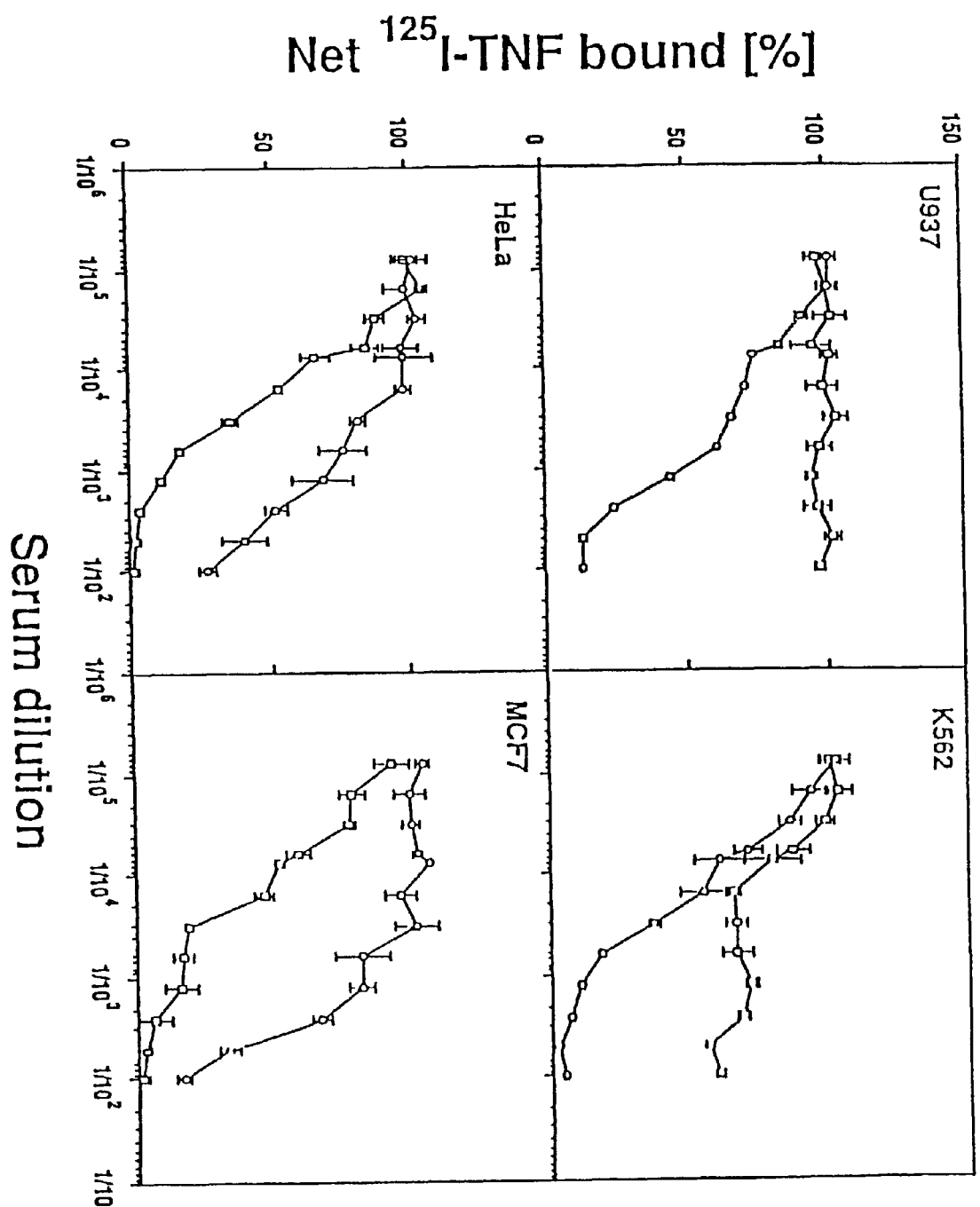
FIG. 5 shows the inhibition of the binding of TNF to different cell lines with antisera to TBP-I and TBP-II.

FIG. 5 shows the inhibition of the binding of radiolabeled TNF to U937, K562, HeLa and MCF7 cells with antisera to TBP-I (○) and TBP-II (□). The net binding observed in the absence of antisera (100%) was in U937 cells—2500 cpm, in K562 cells—1500 cpm, in HeLa cells—2400 cpm and in MCF7 cells—1100 cpm. The results demonstrate that antisera against TBP-I and TBP-II interfere with the binding of TNF to cells, each affecting to different extent cells of different lines. The antiserum against TBP-I inhibits effectively the binding of TNF to HeLa and MCF7 cells, but has no effect on the binding of TNF to U937 cells and only little effect on the binding of TNF to K652 cells. Inversely, the antiserum against TBP-II blocks effectively the binding of TNF to the K562 and U937 cells, but inhibits the binding of TNF to the HeLa and MCF7 cells only at high concentrations. The effect of the antiserum against TBP II on the latter cells could be shown, by competition experiments, at which pure TBP-I and TBP-II were added to the serum, to be due to the presence of contaminating antibodies to TBP-I in this preparation of antiserum to TBP-II.

EXAMPLE 5

Monoclonal Antibodies to TBP-II

Production of the Monoclonal Antibodies

Female Balb/C mice (8 weeks old) were injected with 1 μg purified TBP-II in an emulsion of complete Freund's adjuvant into the hind foot pads, and three weeks later, subcutaneously into the back in incomplete Freund's adjuvant. The other injections were given in weekly intervals, subcutaneously in PBS. Final boosts were given 4 days (i.p.) and 3 days (i.v.) before the fusion with 9.0 μg of TBP-I in PBS. Fusion was performed using NSO/Mr cells and lymphocytes prepared from both the spleen and the local lymphocytes of the hind legs as fusion partners. The hybridomas were selected in DMEM supplemented with HAT, 15% horse serum and gentamycin 2 μg/ml. Hybridomas that were found to produce antibodies to TBP-II were subcloned by the limiting dilution method and injected into Balb/C mice that had been primed with pristane for the production of ascites. Immunoglobulins were isolated from the ascites by ammonium sulfate precipitation (50% saturation) and then dialyzed against PBS containing 0.02% azide. Purity was approximately 60% as estimated by analysis on SDS-PAGE and staining with Coomassie blue. The isotypes of the antibodies were defined with the use of a commercially available ELISA kit (Amersham, U.K.).

Several positive clones were obtained, subcloned for further studies and characterized. Some of the isolated subclones with their isotype and binding of TBP-II in inverted RIA are listed in Table III.

TABLE III

Subclones Producing Monoclonal Antibodies to TBP-II

| Clone Number | Screening with iRIA [CPM] | Screening of subclone with iRIA [CPM] | Isotype |
|---|---|---|---|
| 13.11 | 31800 | 31000 | IgG$_1$ |
| .12 |  | 31500 | IgG$_1$ |
| .13 |  | 31100 | IgG$_1$ |

TABLE III-continued

Subclones Producing Monoclonal Antibodies to TBP-II

| Clone Number | Screening with iRIA [CPM] | Screening of subclone with iRIA [CPM] | Isotype |
|---|---|---|---|
| 14.1 | 15300 | 15400 | $IgG_{2a}$ |
| .6 | | 16200 | $IgG_{2a}$ |
| .7 | | 15300 | $IgG_{2a}$ |
| 20.2 | 12800 | 14200 | $IgG_{2b}$ |
| .5 | | 14300 | $IgG_{2b}$ |
| .6 | | 14800 | $IgG_{2b}$ |
| 22.7 | 20400 | 20000 | $IgG_1$ |
| .8 | | 19300 | $IgG_1$ |
| 27.1 | 18000 | 27000 | $IgG_{2a}$ |
| .3 | | 25000 | $IgG_{2a}$ |
| .9 | | 28000 | $IgG_{2a}$ |
| 32.4 | 11315 | 10900 | $IgG_{2b}$ |
| .5 | | 10700 | $IgG_{2b}$ |
| .6 | | 11200 | $IgG_{2b}$ |
| 33.1 | 18400 | 11400 | $IgG_1$ |
| .3 | | 10500 | $IgG_1$ |
| .4 | | 14800 | $IgG_1$ |
| 36.1 | 27500 | 26600 | $IgG_{2a}$ |
| .5 | | 24900 | $IgG_{2a}$ |
| .6 | | 24900 | $IgG_{2a}$ |
| 41.3 | 13800 | 18100 | $IgG_1$ |
| .7 | | 18100 | $IgG_1$ |
| .10 | | 18800 | $IgG_1$ |
| 67.1 | 16800 | 10900 | $IgG_{2a}$ |
| .16 | | 10800 | $IgG_{2a}$ |
| .17 | | 10900 | $IgG_{2a}$ |
| 70.2 | 15100 | 5100 | $IgG_{2a}$ |
| .3 | | 5200 | $IgG_{2a}$ |
| .4 | | 5300 | $IgG_{2a}$ |
| 77.2 | 15300 | 11800 | $IgG_{2b}$ |
| 78.9 | 25300 | 21400 | $IgG_{2a}$ |
| 82.1 | 17600 | 25900 | $IgG_1$ |
| .4 | | 25700 | $IgG_1$ |
| .10 | | 26400 | $IgG_1$ |
| 86.2 | 8800 | 12200 | $IgG_{2b}$ |
| .5 | | 12600 | $IgG_{2b}$ |
| .11 | | 12800 | $IgG_{2b}$ |
| 19.6 | | 29700 | $IgG_{2a}$ |
| .9 | | 28900 | $IgG_{2a}$ |

Hybridomas TBP-II 13-12 and TBP-II 70-2 were deposited with the Collection Nationale de Cultures de Microorganismes (CNCM), Institut Pasteur, 25, rue du Docteur Roux, 75724 Paris CEDEX 15, France on Mar. 12, 1990, and were assigned No. I-929 and No. I-928, respectively.

EXAMPLE 6

Inverted Radioimmunoassay (iRIA) for the Detection of the Monoclonal Antibodies to TBP-II This assay was used for estimating the level of the anti-TBP antibodies in the sera of the immunized mice and for screening for the production of the antibodies by hybridomas. PVC, 96-well microtiter plates (Dynatech 1-220-25) were coated for 12 hours at 4° C. with affinity purified goat anti mouse F(ab) immunoglobulins (Biomakor, Israel 10 µg/ml in PBS containing 0.02% $NaN_3$), then blocked for 2 hours at 37° C. with 0.5% BSA in PBS supplemented with 0.05% TWEEN 20 polyethylene glycol sorbitan monolaurate non-ionic detergent (Sigma) and 0.02% $NaN_3$ (blocking buffer) and washed 3 times with PBS containing 0.05% TWEEN 20 and 0.02% $NaN_3$ (washing buffer) Serum samples, in serial dilutions, or samples of hybridoma growth media (50 µl) were applied into the wells for 2 hours at 37° C. The plates were rinsed with washing buffer and $^{125}$I-labeled TBP-I (10,000 cpm, in blocking buffer) was applied into the wells. After further incubation of 2 hours at 37° C., the plates were washed and the amount of label which bound to individual wells was determined in the gamma-counter.

EXAMPLE 7

The Use of Anti-TBP-II Antibodies for Affinity Chromatography

Antibodies against TBP-II can be utilized for the purification of TBP-II by affinity chromatography, according to the following procedure. The monoclonal antibodies for affinity chromatography were selected by testing their binding capacity for the radiolabeled antigen in a solid phase radioimmunoassay. Ascites from all hybridomas was purified by ammonium sulfate precipitation at 50% saturation followed by extensive dialysis against PBS. PVC 96-well plates were coated with the purified McAbs, and after blocking the plates with PBS containing 0.5% BSA, 0.05% TWEEN 20 (Sigma) and 0.02% $NaN_3$, the wells were incubated with 50,000 cpm $^{125}$I-TNF for 2 hours at 37° C., then washed and the radioactivity which had bound to each well was quantitated in the gamma-counter. The antibodies with the highest binding capacity were examined for their performance in immunoaffinity chromatography.

Polyacryl hydrazide agarose was used as resin to immobilize the antibodies. The semi-purified immunoglobulins were concentrated and coupled to the resin as specified by Wilchek and Miron, *Methods in Enzymology* 34:72-76, 1979. Three monoclonal antibodies against TBP-I, clones 16, 20, and 34 were tested in these experiments. Antibody columns of 1 ml bed were constructed. Before use, all columns were subjected to 10 washes with the elusion buffer, each wash followed by neutralization with PBS. Then the columns were loaded with 120 ml of concentrated urinary proteins in PBS with 0.02% $NaN_3$. The flow rate of the columns was adjusted to 0.2 to 0.3 ml per minute. After loading, the columns were washed with 50 ml PBS and then eluted with a solution containing 50 mM citric acid, pH 2.5, 100 mM NaCl and 0.02% $NaN_3$. Fractions of 1 ml were collected. Samples of the applied urinary proteins, the last portion of the wash (1 ml) and of each elusion fraction (8 fractions of 1 ml per column) were taken and tested for protein concentration and activity in the bioassay for TBP-II. According to the protein measurements before and after coupling of the antibodies to hydrazide agarose, the amounts of immunoglobulin bound to the columns ranged from 7 to 10 mg/ml agarose. All protein measurements were done according to a micro-fluorescamine method in comparison to a standard solution containing 100 µg BSA/ml (Stein, S. and Moschera, J., *Methods Enzymol.* 79:7-16, 1981).

EXAMPLE 8

Determination of TBP-II Using Anti-TBP-II Antibodies

The levels of TBP-II in the sera of healthy individuals, patients with cancer or systemic lupus erythematosus (SLE) and of pregnant women at term were determined by an ELISA method employing a monoclonal antibody to TBP-II coating the plates. 50 µl of each sample was added and after a 2.5 hour incubation at 37° C. the wells were washed with a solution of PBS, TWEEN 0.05% and sodium azide 0.02%, after which a rabbit anti-TBP-II polyclonal antibody was added for 2.5 hours at 37° C. Then the wells were washed again (no azide) and goat anti-rabbit horseradish peroxidase-coupled antibody was added for 2 hours. Following this incubation and washing, an ABTS buffer was added and optical density (O.D.) read 30 minutes later at 600 nm.

The normal levels of TBP-II in human serum of healthy individuals as determined by the ELISA method are 1.48±0.46 ng/ml.

Figure 6:
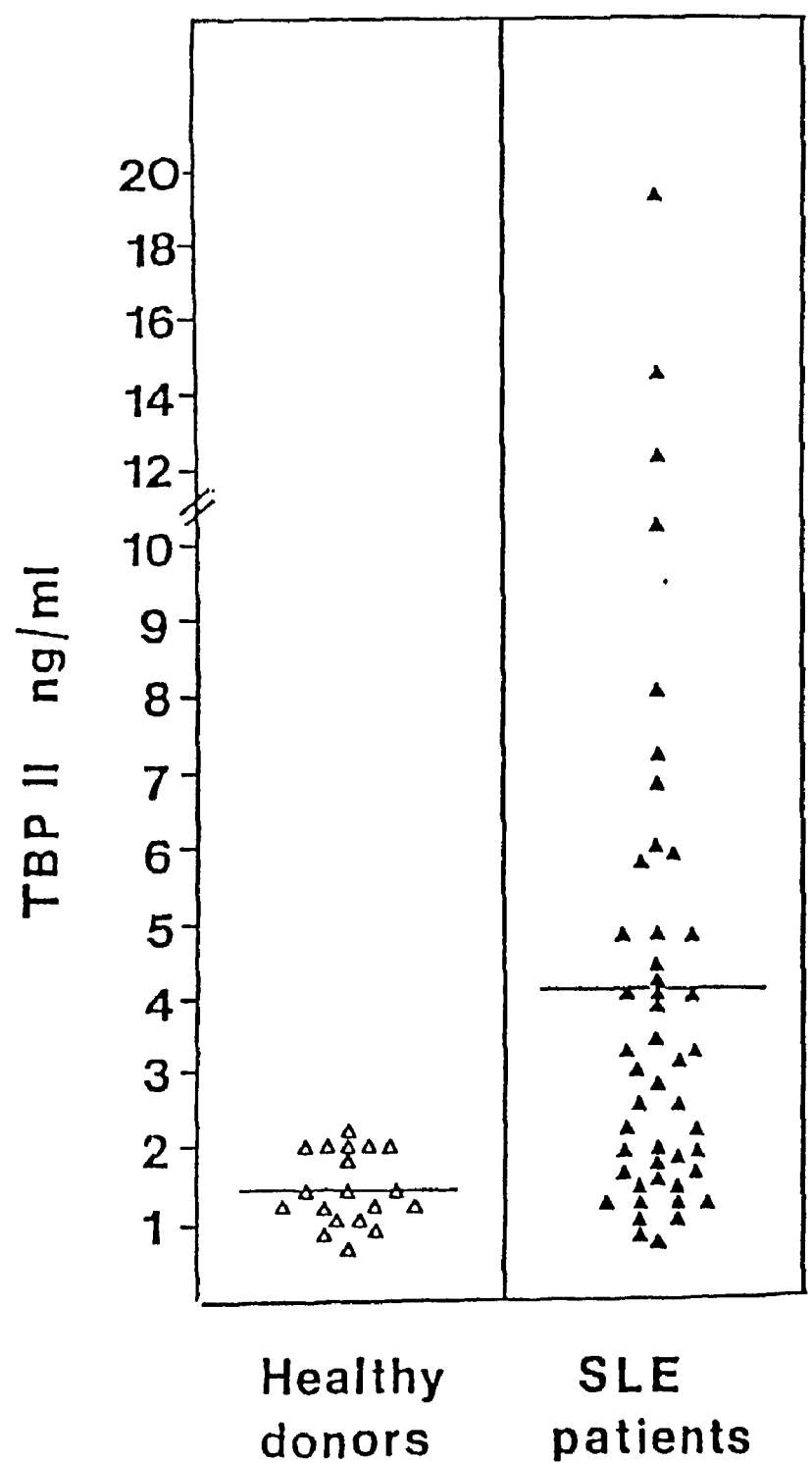
FIG. 6 shows the levels of TBP-II in the sera of healthy individuals and of systemic lupus erythematosus (SLE) patients.

In the sera of 46 patients with Systemic Lupus Erythematosus (SLE), the TBP-II levels were 4.04±3.75 ng/ml, a value highly significant compared to the normal levels (p<0.001). As shown in FIG. 6, 29 out of the 46 patients with SLE had a TBP-II level higher than the mean±2 SD of normal values. We found a highly significant correlation between the TBP-II levels and the disease activity index developed by Symmonds, D. P. M. et al, Quarterly J. of Med. (1988), 69:927-937: r=0.62, p<0.001. A similar correlation was found between TBP-II and the classical marker of SLE activity, the anti-DNA antibodies (r=0.64, p<0.001) and between a major clinical manifestation of SLE activity, i.e., joint pains and TBP-II (r=0.54, p<0.001).

These results indicate that TBP-II may be useful as a sensitive marker of disease activity and a predictor of exacerbations in SLE patients, and thus may be useful in monitoring immune activation related to disease activity in these patients as well as in patients with other autoimmune diseases.

By the above ELISA method, the TBP-II levels in sera of patients with different types of cancer, were examined. In 20 out of 34 patients (58.8%) with different types of cancer, the TBP-II levels were above the normal mean±2 SD. The difference between the TBP-II of cancer patients (4.16±4.08 ng/ml) and healthy controls (1.48±0.46 ng/ml) was highly significant statistically (p<0.001).

These results indicate that TBP-II may prove a useful and universal marker of different types of cancer and may be applied in early detection of this condition. After cancer resection, normalization of TBP-II levels may be a marker of cure of the disease. An increase in TBP-II, after initial normalization, may be an early and sensitive universal marker of disease relapse.

14 pregnant women at term with eclampsia or pre-eclampsia had statistically significant higher TBP-II levels (2.91±0.96 ng/ml) than 16 normotensive pregnant women (1.58±0.52) as determined by the ELISA method (p<0.001).

EXAMPLE 9

Combinations of TBP-II and TNF

In order to examine the activity of TBP-II to prolong beneficial effects of TNF, the following experiments were performed:

FS11 fibroblasts (passage 9) were cultured in microwells (96-well plates) at an initial concentration of 10000 cells/well. After 24 hours, mixtures comprising a constant concentration of rTNF (5 ng/ml) and different concentrations of TBP-II (3 ng to 100 ng/ml) were added to respective wells. To control wells were added medium, rTNF only, or respective TBP-II concentrations, without TNF. After 7 days in culture, the supernatants of the cells were collected and frozen immediately to −20° C. for further determination of residual TNF cytotoxicity and residual TBP-II. After removal of the supernatants, $H^3$-thymidine was added to a FS11 plate for 8 hours while over a "tween" plate a neutral red dye was added.

Figure 7:
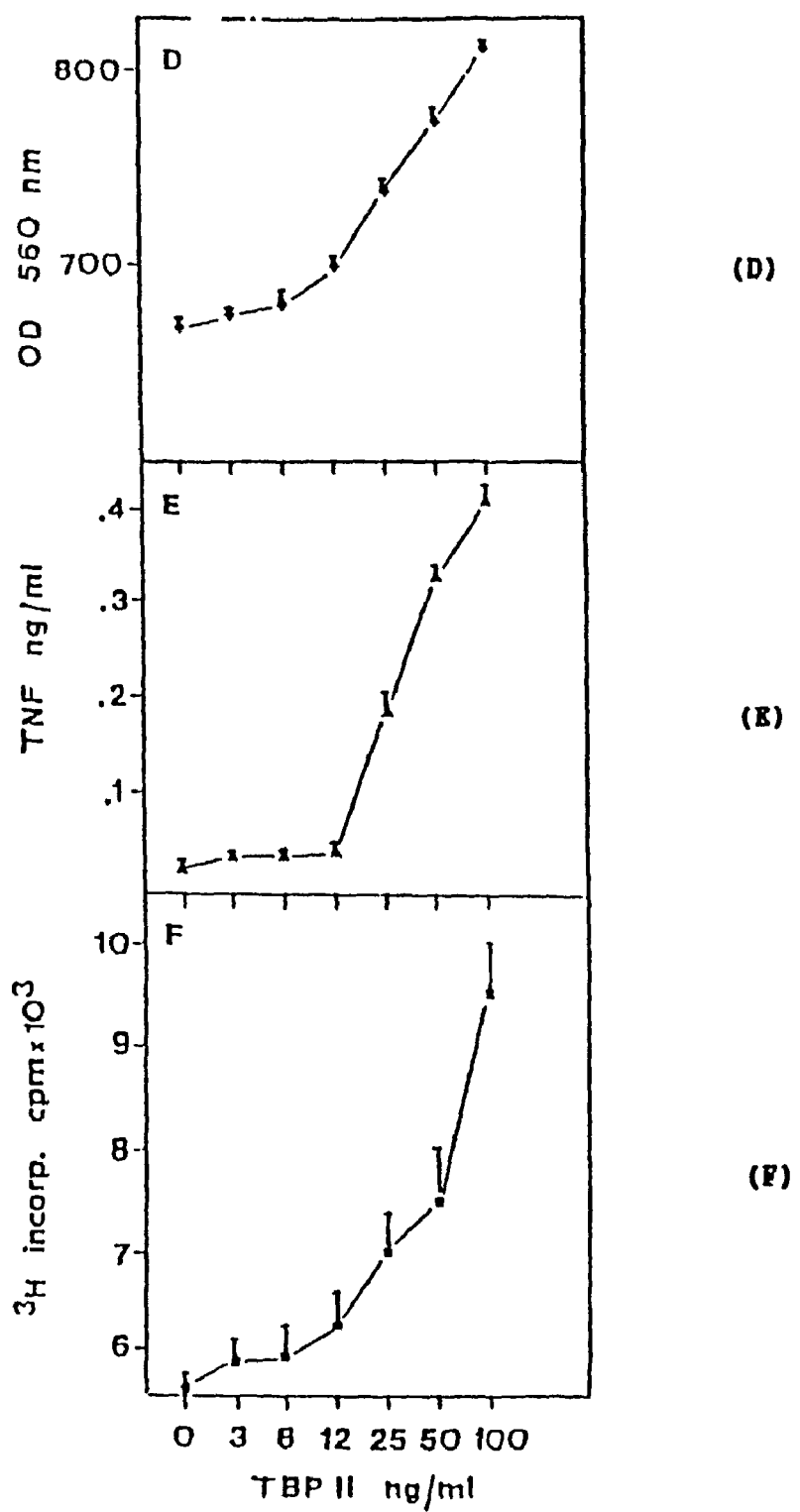
FIG. 7 shows the effects of different concentrations of TBP-II in maintaining prolonged beneficial function of TNF as stimulator of fibroblast growth (FS11 cells).

The results are shown in FIG. 7. FIG. 7 (D) shows that in the presence of TNF 5 ng/ml and increasing TBP-II concentrations, the fibroblast growth was significantly augmented (as determined by the neutral red dye uptake) or by H3-thymidine incorporation (F). Examination of the frozen FS11 supernatants for residual TNF cytotoxicity in a bioassay (the A9 mouse cell line) showed a residual cytotoxicity paralleling the increase in the TBP-II concentrations (E), and suggesting prevention of TNF decay in the system, by TBP-II.

To further explore this phenomenon, rTNF, TBP-II and the respective controls were added to cultured FS11 fibroblasts for 2 hours or 2, 5, 7 and 9 days in different plates. Thereafter, the supernatants were removed and immediately examined for TNF cytotoxicity.

Figure 8:
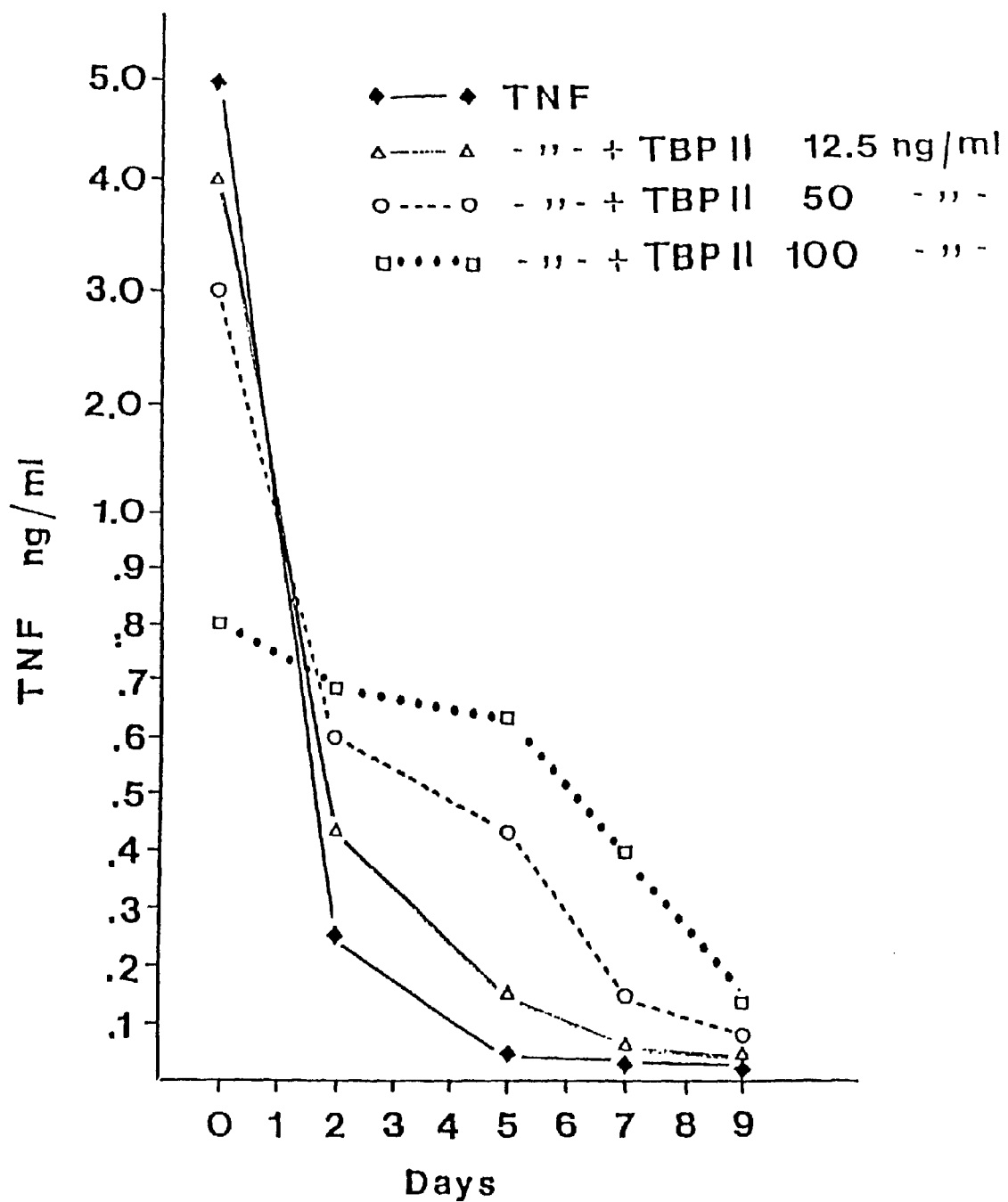
FIG. 8 shows the time-related effects of TBP-II on TNF bioactivity.

As shown in FIG. 8, at 2 hours out of 5 ng rTNF added in the presence of TBP-II, only 0.6 ng remained bioactive, the rest being bound and neutralized by TBP-II. However, between days 2 and 9, while the "lone" rTNF lost its bioactivity rapidly, the detectable cytotoxicity of the rTNF in the presence of TBP-II was 10 times higher. Thus, TBP-II neutralized the high TNF concentration initially, but protected the remaining bioactive TNF from an accelerated loss of its bioactivity. These results indicate that TBP-II binds TNF and prevents its natural decay or loss of activity, thus being useful as a carrier to prolong TNF beneficial effects.

EXAMPLE 10

Epitope Mapping of TBP-II by Cross Competition Analysis with Monoclonal Antibodies (mAbs) to TBP-II PVC 96-well microtiter plates were coated as described above, with purified mAbs to TBP-II (25 µg/ml) produced in Example 5. Following rinsing and blocking, samples of $^{125}$I-labeled TBP-II (100,000 cpm per well) which had been pre-incubated for 2 hours, at 37° C. with the same or a different monoclonal antibody to TBP-II (at 1 µg/ml) were put into the wells; the plates were incubated overnight at 4° C., washed and the radioactivity bound to each well was determined by gamma-counting. The results are expressed as percent of the control values (TBP-II binding in the absence of competing mAbs).

The results are depicted in Table IV. The monoclonal antibodies are indicated by the clone numbers in the first row and in left column. Low percent binding values indicate that the two antibodies compete for each other's epitope on TBP-II, while higher values indicate that they bind to different epitopes. Non-competitive antibodies are suitable for use in double-sandwich ELISA, e.g., clones 13 and 70.

TABLE IV

| Cross-Competition Analysis with Monoclonal Antibodies to TBP-II | | | | | | | | | | | | | | | |
|---|---|---|---|---|---|---|---|---|---|---|---|---|---|---|---|
| | 13 | 14 | 19 | 20 | 22 | 27 | 32 | 33 | 36 | 41 | 67 | 70 | 77 | 78 | 82 | 86 |
| 13 | 4 | 64 | 53 | 73 | 31 | 51 | 161 | 35 | 177 | 72 | 131 | 128 | 77 | 102 | 50 | 101 |
| 14 | 119 | 20 | 90 | 13 | 13 | 84 | 156 | 11 | 132 | 173 | 134 | 113 | 14 | 70 | 89 | 179 |
| 19 | 103 | 28 | 7 | 19 | 11 | 5 | 144 | 11 | 144 | 133 | 179 | 123 | 18 | 5 | 85 | 126 |
| 20 | 119 | 17 | 93 | 14 | 10 | 88 | 149 | 9 | 135 | 170 | 147 | 135 | 16 | 70 | 1101 | 181 |
| 22 | 109 | 26 | 94 | 22 | 13 | 82 | 128 | 12 | 115 | 164 | 136 | 114 | 17 | 68 | 98 | 167 |
| 27 | 106 | 23 | 11 | 27 | 14 | 8 | 145 | 17 | 152 | 133 | 196 | 136 | 24 | 8 | 82 | 125 |

TABLE IV-continued

Cross-Competition Analysis with Monoclonal Antibodies to TBP-II

|  | 13 | 14 | 19 | 20 | 22 | 27 | 32 | 33 | 36 | 41 | 67 | 70 | 77 | 78 | 82 | 86 |
|---|---|---|---|---|---|---|---|---|---|---|---|---|---|---|---|---|
| 32 | 150 | 267 | 150 | 291 | 156 | 186 | 14 | 163 | 139 | 200 | 205 | 18 | 294 | 143 | 103 | 226 |
| 33 | 115 | 19 | 98 | 23 | 16 | 86 | 133 | 12 | 118 | 156 | 120 | 114 | 24 | 78 | 90 | 155 |
| 36 | 155 | 262 | 168 | 271 | 144 | 185 | 167 | 158 | 12 | 169 | 223 | 135 | 265 | 158 | 93 | 150 |
| 41 | 117 | 119 | 119 | 118 | 101 | 109 | 118 | 76 | 93 | 9 | 179 | 107 | 106 | 111 | 8 | 9 |
| 67 | 112 | 138 | 125 | 141 | 125 | 157 | 136 | 107 | 138 | 213 | 30 | 117 | 120 | 127 | 106 | 236 |
| 70 | 150 | 246 | 150 | 255 | 145 | 166 | 4 | 162 | 166 | 217 | 204 | 6 | 232 | 132 | 107 | 234 |
| 77 | 121 | 18 | 98 | 15 | 13 | 78 | 148 | 11 | 145 | 184 | 142 | 132 | 18 | 66 | 103 | 184 |
| 78 | 118 | 20 | 9 | 26 | 10 | 6 | 153 | 13 | 157 | 137 | 183 | 131 | 19 | 6 | 94 | 172 |
| 82 | 107 | 110 | 130 | 116 | 112 | 121 | 128 | 89 | 90 | 8 | 162 | 102 | 121 | 113 | 8 | 7 |
| 86 | 122 | 181 | 125 | 166 | 126 | 129 | 131 | 120 | 86 | 18 | 253 | 109 | 152 | 125 | 20 | 17 |
| 100% value | 31582 | 3958 | 2057 | 5437 | 4947 | 17395 | 25923 | 3525 | 6368 | 8042 | 4368 | 24113 | 5887 | 22222 | 11608 | 9703 |

What is claimed is:

1. An isolated DNA molecule comprising the DNA sequence of SEQ ID NO:7.

2. A replicable expression vehicle comprising the DNA molecule of claim 1 and capable, in a transformant host cell, of expressing said polypeptide.

3. A host cell selected from the group consisting of a prokaryotic and a eukaryotic cell transformed with the replicable expression vehicle of claim 2.

4. A process for producing a polypeptide, comprising the steps of: (a) culturing a transformant host cell according to claim 3 in a suitable culture medium, and (b) isolating said polypeptide.

* * * * *

UNITED STATES PATENT AND TRADEMARK OFFICE
CERTIFICATE OF CORRECTION

| | | |
|---|---|---|
| PATENT NO. | : 8,138,323 B2 | Page 1 of 1 |
| APPLICATION NO. | : 10/319536 | |
| DATED | : March 20, 2012 | |
| INVENTOR(S) | : Wallach et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2177 days.

Signed and Sealed this
Eleventh Day of December, 2012

David J. Kappos
*Director of the United States Patent and Trademark Office*

```
                            SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: synthetic

<400> SEQUENCE: 1

Asp Ser Val Cys Pro
1               5

<210> SEQ ID NO 2
<211> LENGTH: 30
<212> TYPE: PRT
<213> ORGANISM: Artificial Sequence
<220> FEATURE:
<223> OTHER INFORMATION: synthetic

<400> SEQUENCE: 2

Ala Gln Val Ala Phe Thr Pro Tyr Ala Pro Glu Pro Gly Ser Thr Cys
1               5                   10                  15

Arg Leu Arg Glu Tyr Tyr Asp Gln Thr Ala Gln Met Cys Cys
            20                  25                  30

<210> SEQ ID NO 3
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fraction 50 (Figure 3)

<400> SEQUENCE: 3

Leu Arg Val Tyr Tyr Asp Ala Thr Ala Gln Met Cys Cys
1               5                   10

<210> SEQ ID NO 4
<211> LENGTH: 15
<212> TYPE: PRT
<213> ORGANISM: Artificial Sequence
<220> FEATURE:
<223> OTHER INFORMATION: synthetic
<220> FEATURE:
<221> NAME/KEY: misc_feature
```

-continued

```
<223> OTHER INFORMATION: Fraction 53 (second) (Figure 3)

<400> SEQUENCE: 4

Val Ala Phe Thr Pro Tyr Ala Pro Glu Pro Gly Ser Thr Cys Arg
1               5                   10                  15

<210> SEQ ID NO 5
<211> LENGTH: 13
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fraction 60 (Figure 3)

<400> SEQUENCE: 5

Ile Cys Thr Cys Arg Pro Gly Trp Tyr Cys Ala Pro Leu
1               5                   10

<210> SEQ ID NO 6
<211> LENGTH: 19
<212> TYPE: PRT
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: Fraction 84 (Figure 3)

<400> SEQUENCE: 6

Thr Ser Asp Thr Val Cys Asp Ser Cys Glu Asp Ser Thr Tyr Thr Gln
1               5                   10                  15

Leu Trp Asn

<210> SEQ ID NO 7
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: n is A or G or C or T.
<220> FEATURE:
<221> NAME/KEY: misc_feature
<222> LOCATION: (6)..(6)
<223> OTHER INFORMATION: n is A or G or C or T.
<220> FEATURE:
<221> NAME/KEY: misc_feature
<222> LOCATION: (12)..(12)
<223> OTHER INFORMATION: n is A or G or C or T.
<220> FEATURE:
<221> NAME/KEY: misc_feature
<222> LOCATION: (15)..(15)
<223> OTHER INFORMATION: n is A or G or C or T.
<220> FEATURE:
<221> NAME/KEY: misc_feature
<222> LOCATION: (21)..(21)
<223> OTHER INFORMATION: n is A or G or C or T.
<220> FEATURE:
<221> NAME/KEY: misc_feature
<222> LOCATION: (24)..(24)
<223> OTHER INFORMATION: n is A or G or C or T.
<220> FEATURE:
<221> NAME/KEY: misc_feature
<222> LOCATION: (25)..(27)
<223> OTHER INFORMATION: Residues at positions 25-27 can be either TCN
      or AGY, where n is A or G or C or T.
<220> FEATURE:
<221> NAME/KEY: misc_feature
<222> LOCATION: (30)..(30)
```

-continued

<223> OTHER INFORMATION: n is A or G or C or T.

<400> SEQUENCE: 7
acnccntayg cnccngarcc nggnnnnacn                30